US00PP09931P

United States Patent [19]

Bridges

[11] Patent Number: Plant 9,931

[45] Date of Patent: Jun. 24, 1997

[54] MINIATURE ROSE PLANT NAMED 'BRITRICK'

[76] Inventor: Dennis A. Bridges, 2734 Toney Rd., Lawndale, N.C. 28090

[21] Appl. No.: 600,224

[22] Filed: Feb. 12, 1996

[51] Int. Cl.[6] ..... A01H 5/00

[52] U.S. Cl. ..... Plt./7.1

[58] Field of Search ..... Plt./7.1, 10, 9

*Primary Examiner*—Howard J. Locker

[57] ABSTRACT

A new and distinct variety of miniature rose plant characterized by a profusion of exhibition form blooms that ae an unusual combination of colors, consisting of red and light pink with a strong fruity fragrance, on a strong plant with exceptional disease resistance.

1 Drawing Sheet

FIELD OF THE INVENTION

The present invention relates to a new and distinct variety of miniature rose plant which has been given the international variety recognition designation 'Britrick', and is to be marketed in this country under the synonym 'Trickster'.

PLANTS RELATED TO THE INVENTION

The plant of this invention was originated as a result of a planned breeding program and controlled crossing which has as the seed parent the miniature rose cultivar 'Jennifer' (U.S. Pat. No. P.P. 5,857) and as the pollen parent miniature rose cultivar 'Red Beauty' U.S. Pat. No. P.P. 5,115). The plant of the invention was a selection from the progeny of the stated cross, and has been asexually reproduced by the taking and rooting of stem cuttings. Such asexual reproduction as performed at Lawndale, N.C., has shown conclusively that the characteristic and distinctive features of the plant come true to form and are faithfully transmitted through succeeding propagations, thus establishing that 'Britrick' is stable.

SUMMARY OF THE INVENTION

Among the new and novel characteristics which are possessed by this plant, singly and in combination, which distinguish it from its parents and from all other miniature rose cultivars of which I am aware are:

1. Blooms of unusual red and light pink coloration that are well formed, blemish resistant, and show exceptional form and substance;

2. Abundant blooms which are borne singly, and in clusters of up to 5 blooms, on strong stems of from 5 to 7 inches in length;

3. A strong, fruity fragrance;

4. An abundance of glossy, medium green foliage which pleasingly contrasts with an highlights the blooms; and 5. Higher than usual disease resistance to common rose diseases with a higher than usual level of vigor, and growing to a height which is typical of roses of this market class to produce a plant which attractively appoints the home garden while providing cut flowers of exhibition form and quality.

BRIEF DESCRIPTION OF THE DRAWING

The single sheet of the accompanying drawing is a photographic illustration which shows foliage and typical specimens of the flowers of the new variety in different stages of development. Colors illustrated are as accurate and true as is reasonably possible to attain in color illustrations of this type. In this regard, it should be noted that the apparent flecking on the upper surface of the petals is not a characteristic feature of the plant and may be due to reflectance. However, some flecking does appear on the under side of the petals as they begin to open.

DETAILED BOTANICAL DESCRIPTION OF THE PLANT

The following is a detailed botanical description of my new variety of miniature rose, with color terminology in accordance with The *Royal Horticultural Society Colour Chart* (R.H.S.C.C.), except where common dictionary terms of color definition are employed.

Type: Hardy dwarf, bushy, compact, seeding greenhouse, outdoors, cut flower, garden decoration, potted plant.
Commercial class: Miniature.
International recognition name: 'Britrick'.
Commercial synonym: 'Trickster'.

The following observations were made from specimens grown outdoors at Cleveland County, N.C. USA, in June 1995.

The Flower

Blooming Habit: Continuous.
Bud:
- *Size.*—Medium.
- *Length.*—1½ cm just before opening.
- *Form.*—Urn shaped.
- *Color.*—When sepals first divide — Near 36D with flecks of near 46D. When petals begin to unfurl — Inside: Near 46B. When half-blown — Near 46B. Reverse side of petals: Near 56D with flecks of 46B.

Sepals: Slender with several appendages longer than the bud.
Peduncle: About 1 inch in length, Near to 146D, strong and erect.
Bloom:
- *Size.*—About 2¼ inches in diameter when fully expanded.
- *Borne.*—Singly and in clusters of up to 5 blooms.
- *Form.*—High-centered booms reflex symmetrically, opening flat and loosely rolled out.

Petalage: About 28 to 32.
- *Color.*—During the first two days: Inner petals at center of flower: Near to 46B. Outer Petals: Near to 46B. Base of petals (point of attachment): Near to 7B. Reverse of petals: Near to 56D, with edging and flecks near 46B. General tonality from a distance: Red, near to 46B with reverse having shades near to 56D and 46B.

*Color change.*—As bloom ages it stays the same color, near to 46B. General Tonality: Red, near to 46B with some shades of near to 56D showing on petals. After 3 or more days: Near to 46B with little other color showing on petals.

Petals:

*Texture.*—Thick, with good substance.

*Appearance.*—Velvety inside, satiny outside.

*Form.*—Urn-shaped, curling gently as bloom opens.

*Arrangement.*—Regular.

*Petaloids in center.*—Few.

*Persistence.*—Petals drop off cleanly.

*Fragrance.*—Strong and fruity.

*Lasting quality.*—Flower lasts 3–5 days on the plant, and 2–3 days as a cut flower.

Reproductive Organs

Stamens, filaments and anthers:

*Arrangement.*—Regularly arranged around styles.

*Color.*—Yellow, near 16B.

*Pollen.*—Golden yellow, near 18A.

Styles: Of uneven length, thin.

Stigmas: Near 16C in color.

Hips: Globular in shape.

*Color.*—Medium green, near 143C.

*Seeds.*—Do protrude.

The Plant

Form: Slightly spreading, compact.

Growth: Vigorous, Uniform branching.

Height: About 16 to 20 inches when mature.

Foliage: Compound, 5 or 7 leaflets.

*Size.*—Medium for a miniature, each leaf is 3–4 cm in length.

*Quantity.*—Abundant.

*Color.*—New Foliage: Upper side is a combination of near to 199B and 195A. Under side is light green, near 185D. Old Foliage: Upper side is dark green, near 138B. Under side is lighter green, near 138C.

*Shape.*—Oval, pointed.

*Texture.*—Upper side is glossy. Under side is smooth.

*Edge.*—Serrated.

*Serration.*—Regular.

*Leaf stem.*—Upper side is near 146D in color. Under side is near 146D in color.

*Stipules.*—Medium length, slightly bearded.

*Disease resistance.*—Blackspot-good. Mildew-good. Rust-good.

Wood:

*New wood.*—Near 144A in color. Bark is smooth.

*Old wood.*—Near 143A in color. Bark is smooth.

Thorns: Ordinary quantity, base flat, medium length. Color when young is near 39B.

*Position.*—Irregular.

Prickles: None.

Winter hardiness: Winter hardy with little die back.

I claim:

1. A new and distinct variety of rose plant of the miniature rose class, substantially as herein shown and described, and characterized particularly as to novelty by its abundance of exhibition quality blooms of an unusual and striking combination of red and light pink, strong fruity fragrance, firm thick petals, blooms being borne singly and in sprays of up to 5, a medium tall plant with glossy medium green foliage, said plant being easy to propagate from cuttings, and said blooms being relatively long lasting both on the plant and as cut flowers.

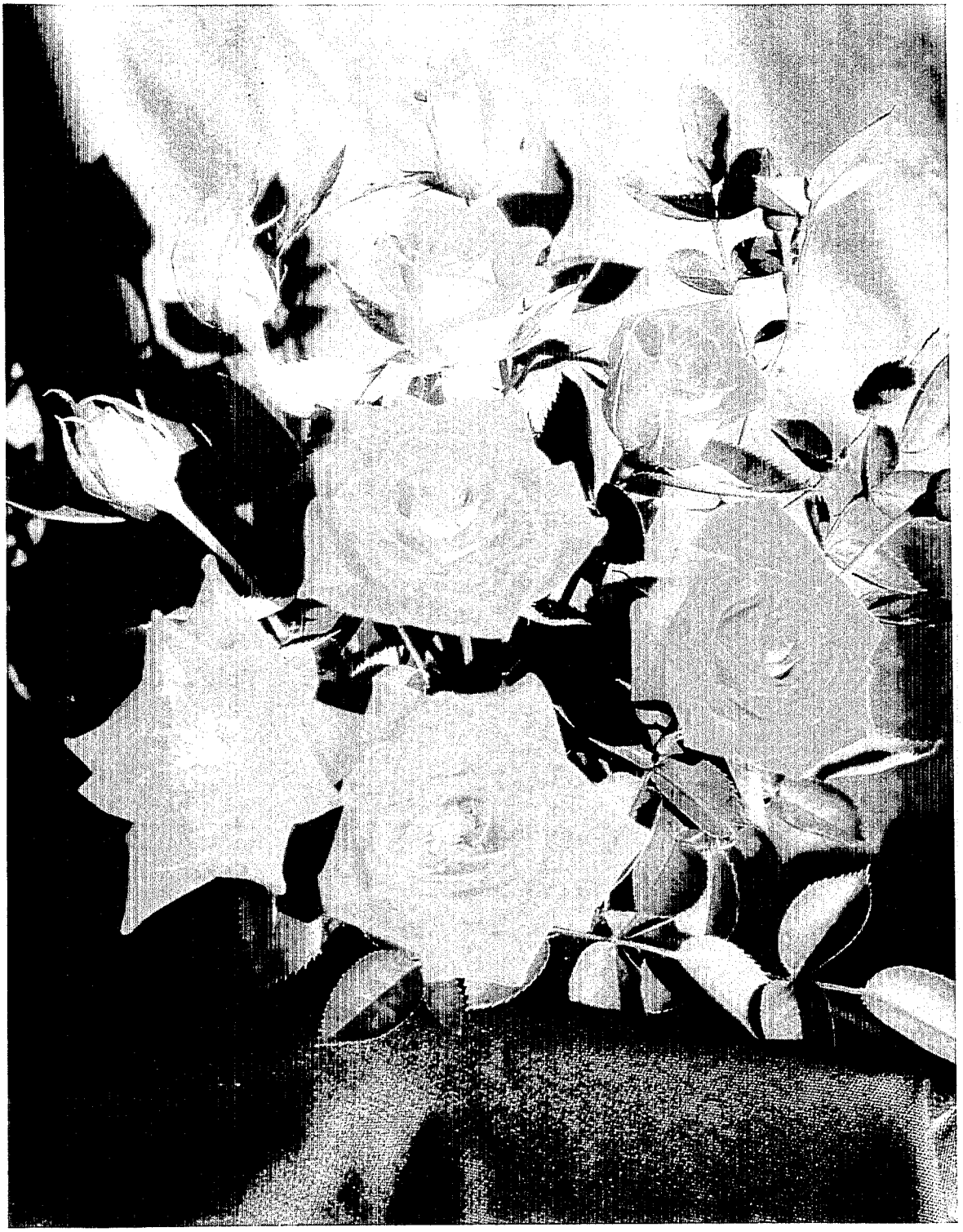

* * * * *